US012046338B2

(12) United States Patent
Akmaev et al.

(10) Patent No.: US 12,046,338 B2
(45) Date of Patent: Jul. 23, 2024

(54) ASSESSING RESPONSIVENESS TO THERAPY

(71) Applicant: Scipher Medicine Corporation, Waltham, MA (US)

(72) Inventors: Viatcheslav R. Akmaev, Sudbury, MA (US); Lixia Zhang, Waltham, MA (US)

(73) Assignee: SCIPHER MEDICINE CORPORATION, Waltham, MA (US)

( * ) Notice: Subject to any disclaimer, the term of this patent is extended or adjusted under 35 U.S.C. 154(b) by 0 days.

(21) Appl. No.: 18/504,564

(22) Filed: Nov. 8, 2023

(65) Prior Publication Data
US 2024/0079107 A1  Mar. 7, 2024

Related U.S. Application Data

(63) Continuation of application No. PCT/US2022/028593, filed on May 10, 2022.

(60) Provisional application No. 63/188,427, filed on May 13, 2021.

(51) Int. Cl.
*G16H 20/00* (2018.01)
(52) U.S. Cl.
CPC .................. *G16H 20/00* (2018.01)
(58) Field of Classification Search
CPC ........ G16H 20/00; G16H 20/10; G16H 50/30; G16H 50/50
See application file for complete search history.

(56) References Cited

U.S. PATENT DOCUMENTS

| | | | |
|---|---|---|---|
| 10,490,309 B1 * | 11/2019 | McNair | G16H 50/20 |
| 10,614,919 B1 * | 4/2020 | Yedwab | G16H 10/60 |
| 11,205,516 B2 * | 12/2021 | Lieberman | G06N 3/045 |
| 11,551,817 B2 * | 1/2023 | Myers | G16H 50/20 |
| 2004/0267570 A1 * | 12/2004 | Becker | A61B 5/165 |
| | | | 705/2 |
| 2007/0099239 A1 * | 5/2007 | Tabibiazar | G16B 40/20 |
| | | | 435/7.1 |
| 2008/0166348 A1 * | 7/2008 | Kupper | A61K 39/092 |
| | | | 424/136.1 |
| 2009/0182581 A1 * | 7/2009 | Ueno | G06Q 10/10 |
| | | | 703/2 |
| 2009/0299645 A1 * | 12/2009 | Colby | G16B 20/10 |
| | | | 506/7 |

(Continued)

FOREIGN PATENT DOCUMENTS

| WO | WO-2019178546 A1 | 9/2019 |
|---|---|---|
| WO | WO-2020102043 A1 | 5/2020 |

(Continued)

OTHER PUBLICATIONS

Abraham et al., Inflammatory Bowel Disease. N Engl J Med 361(21):2066 (2009).

(Continued)

*Primary Examiner* — Ryan W Sherwin
(74) *Attorney, Agent, or Firm* — WILSON SONSINI GOODRICH & ROSATI

(57) ABSTRACT

Presented herein are systems and methods for validating and/or developing (e.g., training) a classifier that identifies a subject suffering from an autoimmune disease (e.g., rheumatoid arthritis, RA) as likely responsive or likely non-responsive to a therapy (e.g., an anti-TNF therapy) prior to any administration of the therapy to the subject.

12 Claims, 10 Drawing Sheets

(56) References Cited

U.S. PATENT DOCUMENTS

| | | | |
|---|---|---|---|
| 2009/0318775 A1* | 12/2009 | Michelson | G16B 40/30 |
| | | | 600/300 |
| 2013/0124224 A1 | 5/2013 | Srinivasan et al. | |
| 2014/0141986 A1* | 5/2014 | Spetzler | G01N 33/50 |
| | | | 435/7.1 |
| 2015/0100286 A1* | 4/2015 | Williams | G16B 5/00 |
| | | | 703/2 |
| 2015/0376710 A1 | 12/2015 | Hatzis et al. | |
| 2016/0078182 A1 | 3/2016 | Allen et al. | |
| 2016/0246930 A1* | 8/2016 | Raha | G16H 50/70 |
| 2017/0270254 A1 | 9/2017 | Guney et al. | |
| 2018/0068083 A1 | 3/2018 | Cohen et al. | |
| 2018/0330824 A1 | 11/2018 | Athey et al. | |
| 2019/0237173 A1* | 8/2019 | Schaefer | G16H 20/00 |
| 2019/0279736 A1* | 9/2019 | Vishnudas | G01N 33/5008 |
| 2019/0333636 A1* | 10/2019 | Bennett | G16H 50/00 |
| 2020/0075164 A1* | 3/2020 | Lieberman | G06N 3/084 |
| 2020/0111021 A1 | 4/2020 | Keyngnaert et al. | |
| 2020/0185099 A1* | 6/2020 | Britt | G16H 50/70 |
| 2021/0174958 A1* | 6/2021 | Drake | G06N 20/10 |
| 2021/0217529 A1* | 7/2021 | Myers | G16H 40/20 |
| 2022/0233135 A1* | 7/2022 | Shelton, IV | A61B 5/4266 |
| 2022/0392564 A1 | 12/2022 | Ghiassian et al. | |
| 2022/0406405 A1* | 12/2022 | Durham | G16H 20/00 |
| 2023/0001234 A1* | 1/2023 | Peri | A61N 5/1031 |

FOREIGN PATENT DOCUMENTS

| | | |
|---|---|---|
| WO | WO-2020264426 A1 | 12/2020 |
| WO | WO-2022240875 A1 | 11/2022 |
| WO | WO-2022271717 A1 | 12/2022 |
| WO | WO-2022271724 A1 | 12/2022 |

OTHER PUBLICATIONS

Anaya et al., The autoimmune tautology: from polyautoimmunity and familial autoimmunity to the autoimmune genes. Autoimmune Dis 2012:297193 (2012).

Arijs et al.: Mucosal Gene Expression of Antimicrobial Peptides in Inflammatory Bowel Disease Before and After First Infliximab Treatment. PloS one. 4(11):e7984-10 (2009).

Barabasi et al., Network medicine: a network-based approach to human disease. Nat. Rev. Genet 12(1):56-68 (2011).

Barrett et al., NCBI GEO: archive for functional genomics data sets-update. Nucleic acids research 41:D991-D995 (2012).

Bassetti et al., *Staphylococcus aureus* in patients with rheumatoid arthritis under conventional and anti-tumor necrosis factor-alpha treatment. J Rheumatol 32(11):2125 (2005).

Benjamini et al., Controlling the false discovery rate: a practical and powerful approach to multiple testing. Journal of the Royal statistical society: series B (Methodological) 57:289 (1995).

Bischoff et al., Intestinal permeability—a new target for disease prevention and therapy. BMC Gastroenterol 14:189 (2014).

Bjerrum et al., Transcriptional analysis of left-sided colitis, pancolitis, and ulcerative colitis-associated dysplasia. Inflamm Bowel Dis20:2340-2352 (2014).

Bravo et al., Extraction of relations between genes and diseases from text and large-scale data analysis: implications for translational research. BMC Bioinformatics 16:55 (2015).

Breitling et al. Rank products: a simple, yet powerful, new method to detect differentially regulated genes in replicated microarray experiments. FEBS Lett 573(1-3):83-92 (2004).

Buniello et al., The NHGRI-EBI GWAS Catalog of published genome-wide association studies, targeted arrays and summary statistics 2019. Nucleic Acids Res 47:D1005 (2019).

Cao et al., Going the distance for protein function prediction: a new distance metric for protein interaction networks. PLOS One 8(10):e76339 (2013).

Caruso et al., A review of COVID-19 biomarkers and drug targets: resources and tools. Brief Bioinform. 22(2):701-713 (2021).

Cheng et al., Network-based approach to prediction and population-based validation of in silico drug repurposing. Nat Commun 9(1):2691 (2018).

Cojocaru et al., Multiple autoimmune syndrome. Maedica 5:132 (2010).

Corsello et al., The Drug Repurposing Hub: a next-generation drug library and information resource. Nature Med 23:405 (2017).

Costa et al., Transcriptome analysis of the oil-rich seed of the bioenergy crop *Jatropha curcas* L. BMC Genomics 11:462 (2010).

Danese et al., Targeting S1P in inflammatory bowel disease: new avenues for modulating intestinal leukocyte migration. J Crohns Colitis 12(Supp_2):S678-S686 (2018).

Eisenberg et al., Human housekeeping genes, revisited. Trends in Genetics 29(10):569-574 (2013).

Ferrero et al., In silico prediction of novel therapeutic targets using gene-disease association data. J Transl Med 15(1):182 (2017).

Frohlich et al., From hype to reality: data science enabling personalized medicine BMC Med, 16(1):150 (2018).

Goh et al., The human disease network. PNAS USA 104:8685 (2007).

Guney et al., Network-based in silico drug efficacy screening. Nat Commun 7:10331 (2016).

Haupt et al., Drug promiscuity in PDB: protein binding site similarity is key. PLoS One 8:e65894 (2013).

Hazel et al., Emerging treatments for inflammatory bowel disease. Ther Adv Chronic Dis 11:2040622319899297 (2020).

Hruz et al., Genevestigator v3: a reference expression database for the meta-analysis of transcriptomes. Adv Bioinformatics 2008:420747 (2008).

Hua et al., TLR signaling in B-cell development and activation. Cell Mol Immunol 10(2):103-106 (2013).

Ideker et al., Protein networks in disease. Genome Res 18:644 (2008).

Isik et al., Drug target prioritization by perturbed gene expression and network information. Sci Rep 5:17417 (2015).

Jeon et al., A systematic approach to identify novel cancer drug targets using machine learning, inhibitor design and high-throughput screening. Genome Med 6:57 (2014).

Kanehisa et al. KEGG: Kyoto Encyclopedia of Genes and Genomes. Nucleic Acids Res 28:27-30 (2000).

Kashani et al., The Expanding Role of Anti-IL-12 and/or Anti-IL-23 Antibodies in the Treatment of Inflammatory Bowel Disease. Gastroenterol Hepatol 15:255-265 (2019).

Katsila et al., Computational approaches in target identification and drug discovery. Comput Struct Biotechnol J 14:177-184 (2016).

Kim et al., An analysis of disease-gene relationship from Medline abstracts by DigSee. Sci Reps 7:40154 (2017).

Kinugasa et al., Claudins regulate the intestinal barrier in response to immune mediators. Gastroenterol 118:1001-1011 (2000).

Knox et al., DrugBank 3.0: a comprehensive resource for 'omics' research on drugs. Nucleic Acids Res 39:D1035 (2010).

Kuleshov et al., Enrichr: a comprehensive gene set enrichment analysis web server 2016 update. Nucleic Acids Res 44:W90-W97 (2016).

Landrum et al., ClinVar: improving access to variant interpretations and supporting evidence. Nucleic Acids Res 46:D1062 (2018).

Leiserson et al., Pan-cancer network analysis identifies combinations of rare somatic mutations across pathways and protein complexes. Nature Genet 47:106 (2015).

Lu et al., Sampling Connected Induced Subgraphs Uniformly at Random. International Conference on Scientific and Statistical Database Management, Springer pp. 195-212 (2012).

Maloy et al., IL-23 and Th17 cytokines in intestinal homeostasis. Mucosal immunology 1:339 (2008).

Mamoshina et al., Machine learning on human muscle transcriptomic data for biomarker discovery and tissue-specific drug target identification. Frontiers Genet 9:242 (2018).

Mathur et al. Personalized medicine could transform healthcare. Biomed. Rep., 7:3-5 (2017).

McInnes et al.: UMAP: Uniform Manifold Approximation and Projection for Dimension Reduction arXiv:1802.03426, pp. 1-63 doi:10.48550/arxiv.1802.03426 (2020).

(56) References Cited

OTHER PUBLICATIONS

Menche et al., Uncovering disease-disease relationships through the incomplete interactome. Science 347(6224):1257601 (2015).
Montero-Melendez et al., Identification of novel predictor classifiers for inflammatory bowel disease by gene expression profiling. PloS One 8:e76235 (2013).
O'Neill et al., The history of Toll-like receptors—redefining innate immunity. Nature Reviews Immunology 13:453 (2013).
Park et al., Anti-integrin therapy for inflammatory bowel disease. World J Gastroenterol 24:1868-1880 (2018.
Park et al., Current and emerging biologics for ulcerative colitis. Gut and liver 9:18-27 (2015).
Pavlidis et al., I_MDS: an inflammatory bowel disease molecular activity score to classify patients with differing disease-driving pathways and therapeutic response to anti-TNF treatment. PLoS Comput Biol 15:e1006951 (2019).
PCT/US2022/034368 International Invitation to Pay Additional Fees dated Sep. 8, 2022.
PCT/US2022/034368 International Search Report and Written Opinion dated Nov. 15, 2022.
PCT/US2022/034375 International Search Report and Written Opinion dated Sep. 21, 2022.
Planell et al., Transcriptional analysis of the intestinal mucosa of patients with ulcerative colitis in remission reveals lasting epithelial cell alterations. Gut 62:967 (2013).
Rappaport et al., MalaCards: an integrated compendium for diseases and their annotation. Database (Oxford) 2013:bat018 (2013).
Rolland et al., A proteome-scale map of the human interactome network. Cell 159:1212 (2014).
Rutgeerts et al. Infliximab for induction and maintenance therapy for ulcerative colitis. N Engl J Med. 353(23):2462-76 (2005).
Shapiro et al., Immunoglobulin A targets a unique subset of the microbiota in inflammatory bowel disease. Cell Host Microbe 29(1):83-93.e3 (2021).
Sharma et al. A disease module in the interactome explains disease heterogeneity, drug response and captures novel pathways and genes in asthma. Hum Mol Genet. 24(11):3005-20 (2015).
Sánchez-Muñoz et al., Transcript levels of Toll-Like Receptors 5, 8 and 9 correlate with inflammatory activity in Ulcerative Colitis. BMC Gastroenterol 11:138 (2011).
Subramanian et al. A Next Generation Connectivity Map: L1000 Platform and the First 1,000,000 Profiles. Cell 171:1437-1452 (2017).
Subramanian et al. Gene set enrichment analysis: a knowledge-based approach for interpreting genome-wide expression profiles. PNAS USA 102:15545-15550 (2005).
Telesco et al., Gene expression signature for prediction of golimumab response in a phase 2a open-label trial of patients with ulcerative colitis. Gastroenterology 155:1008-1011.e8 (2018).
Toedter et al.: Gene expression profiling and response signatures associated with differential responses to infliximab treatment in ulcerative colitis. Am. J. Gastroenterology; 106(7):1272-1280 (2011).
Troncone et al., Novel therapeutic options for people with ulcerative colitis: an update on recent developments with Janus kinase (JAK) inhibitors. Clin Exp Gastroenterol 13:131 (2020.
Vamathevan et al., Applications of machine learning in drug discovery and development. Nat Rev Drug Discov 18:463 (2019).
Van Kessel et al., Neutrophil-mediated phagocytosis of *Staphylococcus aureus*. Frontiers Immunol 5:467 (2014).
Xu et al., Discovering disease-genes by topological features in human protein-protein interaction network. Bioinformatics 22:2800 (2006).
Yildirim et al., Drug-target network. Nature biotechnology 25:1119 (2007).
Zhao et al., Network-based relating pharmacological and genomic spaces for drug target identification. PloS One 5:e11764 (2010).
Cheung et al. Reliability of joint count assessment in rheumatoid arthritis: a systematic literature review. Semin Arthritis Rheum 43:721-729 (2014).).
Cuppen et al. Personalized biological treatment for rheumatoid arthritis: a systematic review with a focus on clinical applicability. Rheumatology (Oxford) 55(5):826-39 (2016).
Maska et al. Measures of functional status and quality of life in rheumatoid arthritis: Health Assessment Questionnaire Disability Index (HAQ), Modified Health Assessment Questionnaire (MHAQ), Multidimensional Health Assessment Questionnaire (MDHAQ), Health Assessment Questionnaire II (HAQ-II), Improved Health Assessment Questionnaire (Improved HAQ). Rheumatoid Arthritis Quality of Life (RAQOL). Arthritis Care Res (Hoboken) 63 Suppl 11:S4-13 (2011)).
Mellors et al. Clinical validation of a blood-based predictive test for stratification of response to tumor necrosis factor inhibitor therapies in rheumatoid arthritis patients. Network and Systems Medicine 3(1):91-104 (2020).
PCT/US2022/028593 International Search Report and Written Opinion dated Aug. 19, 2022.
Schipper et al. Time to achieve remission determines time to be in remission. Arthritis Res Ther 12(3):R97 (2010).
Tweehuysen et al. Predictive value of ex-vivo drug-inhibited cytokine production for clinical response to biologic DMARD therapy in rheumatoid arthritis. Clin Exp Rheumatol 37(3):367-72 (2019).
Uhlig et al. Test-retest reliability of disease activity core set measures and indices in rheumatoid arthritis. Ann Rheum Dis 68:972-975 (2009).).
U.S. Appl. No. 17/881,441 Office Action dated Dec. 15, 2022.
Van Nies et al. What is the evidence for the presence of a therapeutic window of opportunity in rheumatoid arthritis? A systematic literature review. Ann Rheum Dis 73(5):861-70 (2014).

\* cited by examiner

ASSESSING RESPONSIVENESS TO THERAPY

CROSS-REFERENCE TO RELATED APPLICATIONS

The present application is a continuation of International Application No. PCT/US2022/028593, filed May 10, 2022, which claims priority to U.S. Provisional Application No. 63/188,427, filed May 13, 2021, each of which is incorporated by reference herein in its entirety.

BACKGROUND

Following treatment recommendations, many people with rheumatoid arthritis (RA) begin targeted therapy with TNF inhibitors (e.g., TNFi or anti-TNF therapies), even though inadequate response to TNFi therapies may be widespread. Treatment changes from one medication to the next may be currently fueled by disease-activity measures and eventually result in disease control for most patients; however, this "trial-and-error" approach may waste precious time on ineffective treatments. A delay in reaching treat-to-target goals may have a negative effect on patient burden and, possibly, disease progression.

SUMMARY

Useful predictors for TNFi response may be challenging to identify, but a molecular signature response classifier (MSRC) test may be predictive for inadequate response to TNFi therapies (as described by, for example, Mellors T, Withers J B, Ameli A, et al. Clinical Validation of a Blood-Based Predictive Test for Stratification of Response to Tumor Necrosis Factor Inhibitor Therapies in Rheumatoid Arthritis Patients. *Network and Systems Medicine* 2020; 3(1): 91-104, which is incorporated by reference herein in its entirety). See also International Patent Publication No. WO2019/178546 (Application No. PCT/US2020/039991) and International Patent Publication No. WO2020/264426 (Application No. PCT/US2019/022588), each of which is incorporated by reference herein in its entirety. The impact of such identification has the potential to result in improved patient outcomes, but further improvement in such classifiers may be beneficial, especially for response criteria other than ACR50, and in a stringent treat-to-target setting with lower baseline disease activity.

The present disclosure provides systems and methods for validating and/or developing (e.g., training) a classifier that identifies a subject suffering from a disease (e.g., an autoimmune disease, such as rheumatoid arthritis, RA) as likely responsive or likely non-responsive to an therapy (e.g., anti-TNF therapy) prior to any administration of the therapy to the subject.

There is a need to be able to determine whether a subject (e.g., patient) is responding to particular therapies, e.g., anti-TNF therapies, to avoid risks associated with the medications as well as progression of their disease. The present disclosure encompasses an insight that assessment of certain clinical characteristics, e.g., those clinical characteristics provided by the American College of Rheumatology (ACR) and/or the European League against Rheumatism (EULAR), when incorporated into a classifier, can be used to determine whether a patient is a responder or non-responder to anti-TNF therapy. Among other things, the present disclosure appreciates that clinical characteristics of known responders and non-responders (e.g., patients who have previously been treated with anti-TNF therapy and whose classification as responsive or non-responsive is known, referred to as "prior subjects"), are subjectively assessed, and can vary from patient to patient, and practitioner to practitioner. For example, the present disclosure appreciates that variation may occur in such clinical assessments that may represent inputs external to the patient (e.g., differences in application of an assessment and/or interpretation of a patient characteristic or response). Such variation hinders the ability to determine whether therapy is working, e.g., by confirming improvements in the clinical characteristic scores provided by the ACR and EULAR.

As an example, illustrated herein is the validation of a molecular signature response classifier (MSRC) test taken at baseline (prior to treatment) for identifying those patients who do not meet EULAR good response criteria after six months of TNFi treatment.

In one aspect, the present disclosure provides a computer-implemented method for assessing credibility/confidence of a composite of a plurality of clinical features with inter- and/or intra-individual variability, the method comprising: receiving a set of observed values corresponding to a plurality of clinical features observed in the subject that are part of a composite metric, wherein each of the plurality of clinical features has an observed (and/or derived/derivable) inter- and/or intra-individual variability (e.g., wherein the different clinical features with inter- and/or intra-individual variability are integrated in the composite metric); generating a plurality of simulated clinical measurements corresponding to each of the observed values (e.g., using stochastic simulation e.g., Monte Carlo simulation), wherein said generating is performed using the corresponding observed inter- and/or intra-individual variability of the respective clinical features; and determining a score of other classification of the confidence/credibility of the observed composite metric.

In some embodiments, the composite metric is used in one or more of the following: (i) identifying training/validation sets for building a classifier in diagnostics (e.g., training data for a machine learning algorithm), (ii) biomarker detection, and (iii) clinical trial cohort identification.

In some embodiments, the composite metric comprises ACR50, EULAR, CDAI, or DAS28-crp, where:
(i) ACR50 responder is defined as ≥50% improvement in 28 tender joint count, ≥50% improvement in 28 swollen joint count, and ≥50% improvement in at least three out of five clinical variables (Health Assessment Questionnaire disability index [HAQ-DI], patient pain assessment, patient global assessment, physician global assessment, and serum C-reactive protein level); otherwise ACR50 non-responder,
(ii) EULAR is defined as follows:

| DAS28-CRP at endpoint* | Improvement >1.2 | Improvement >0.6 & ≤1.2 | Improvement ≤0.6 |
|---|---|---|---|
| ≤2.9 | good | moderate | poor |
| >2.9 & ≤4.6 | moderate | moderate | poor |
| >4.6 | moderate | poor | poor |

(iii) CDAI is defined as 28TJC+28SJC+PrGA+PtGA, where 28TJC is 28 tender joint count, 28SJC is 28 swollen joint count, PrGA is provider global assessment of disease activity, and PtGA is patient global assessment of disease activity, and (iv) DAS28-crp is defined as $0.56 \times \sqrt{28TJC} + 0.28 \times \sqrt{28SJC} + 0.36 \times \ln(CRP+1) + 0.014 \times PtGA + 0.96$.

In some embodiments, the method further comprises confirming and/or developing a classifier (e.g., the composite metric) that identifies a person as likely responsive and/or non-responsive to a given therapy.

In some embodiments, the method further comprises identifying one or more biomarkers (e.g., for a diagnostic product) based at least in part on the determined confidence/credibility of the observed composite metric.

In some embodiments, the method further comprises assessing clinical trial data based at least in part on the determined confidence/credibility of the observed composite metric (e.g., assessment of group and/or individual response to therapy for use in drug development and/or approval, e.g., assessment of whether a drug is safe and/or effective).

In another aspect, the present disclosure provides a computer-implemented method for validating and/or developing (e.g., training) a classifier that identifies a subject suffering from a disease as likely responsive or likely non-responsive to a therapy prior to any administration of the therapy to the subject (e.g., wherein the classifier comprises a composite of a plurality of clinical measurements with inter- and/or intra-individual variability and wherein the method comprises assigning a score or otherwise classifying a confidence/credibility of an observed composite clinical measurement for the subject), the method comprising: receiving for each member of a set of subjects (e.g., humans), a set of observed values corresponding to a plurality of clinical measurements observed in the subject, wherein each of the plurality of clinical measurements has an observed (and/or derived/derivable) inter- and/or intra-individual variability; generating for each member of the set of subjects, a plurality of simulated clinical measurements corresponding to each of the observed values (e.g., using stochastic simulation e.g., Monte Carlo simulation) (e.g, wherein the different clinical measurements with inter- and/or intra-individual variability are integrated in a composite metric), wherein the generating is performed using the observed inter- and/or intra-individual variability of each of the plurality of clinical measurements; categorizing each member of the set of subjects as either (i) a high confidence responder or high confidence non-responder to the therapy, or (ii) neither a high confidence responder nor high confidence non-responder to the therapy, wherein the classifying is performed using the plurality of simulated clinical measurements as input to the classifier that identifies a subject suffering from the a disease as likely responsive or likely non-responsive to the therapy prior to any administration of the therapy to the subject; and validating and/or developing (e.g., training) the classifier using data corresponding to the set of subjects categorized in category (i) and rejecting data corresponding to the set of subjects categorized in category (ii).

In another aspect, the present disclosure provides a method of treating a subject suffering from a disease, disorder, or a condition, the method comprising: administering a therapy to the subject who has been assigned a confidence outcome score, wherein the confidence outcome score is derived by: analyzing an observed value of one or more clinical characteristics of the disease, disorder, or condition provided by the subject, wherein each of the one or more clinical characteristics has an observed inter and/or intra-individual variability; calculating a plurality of (e.g., at least 100, 300, 500, 1000, 1500, 2000, or more; e.g., at most about 2000, 1500, 1000, 500, 300, 100, or less) simulated clinical measurements corresponding to each of the observed values (e.g., using stochastic simulation e.g., Monte Carlo simulation), wherein the calculating is performed using the observed inter- and/or intra-individual variability of each of the one or more of clinical characteristics; and generating the confidence outcome score from inputs of each of the plurality of simulated clinical measurements, wherein the subject is administered the therapy if the confidence outcome score is a high confidence outcome score.

In some embodiments, the disease, disorder, or condition comprises an autoimmune disease or a cancer.

In some embodiments the disease, disorder or condition comprises an autoimmune disease. In some embodiments, the autoimmune disease comprises rheumatoid arthritis, ulcerative colitis, Crohn's disease, juvenile arthritis, psoriatic arthritis, plaque psoriasis, or ankylosing spondylitis, or a combination thereof.

In some embodiments, the observed values of one or more clinical characteristics comprises tender joint count, swollen joint count, physician global assessment, patient global assessment, patient pain assessment, CRP, or HAQ-DI, or a combination thereof.

In some embodiments, the therapy comprises anti-TNF therapy. In some embodiments, the anti-TNF therapy comprises infliximab, etanercept, adalimumab, certolizumab pegol, golimumab, or biosimilars thereof, or a combination thereof.

In some embodiments, the therapy comprises an alternative to anti-TNF therapy. In some embodiments, the alternative to anti-TNF therapy comprises rituximab, sarilumab, tofacitinib citrate, lefunomide, vedolizumab, tocilizumab, anakinra, or abatacept, or a combination thereof.

In another aspect, the present disclosure provides a computer-implemented method for validating and/or developing (e.g., training) a classifier that identifies a subject suffering from a disease (e.g., an autoimmune disease, such as rheumatoid arthritis, RA) as likely responsive or likely non-responsive to a therapy (e.g., anti-TNF therapy) prior to any administration of the therapy to the subject, the method comprising: receiving for each member of a set of subjects (e.g, humans), a set of observed values corresponding to a plurality of clinical measurements observed in the subject, wherein each of the plurality of clinical measurements has an observed inter- and/or intra-individual variability; generating for each member of the set of subjects, a plurality of (e.g, at least about 100, 300, 500, 1000, 1500, 2000, or more; e.g., at most about 2000, 1500, 1000, 500, 300, 100, or less) simulated clinical measurements corresponding to each of the observed values (e.g., using stochastic simulation e.g., Monte Carlo simulation), wherein the generating is performed using the observed inter- and/or intra-individual variability of each of the plurality of clinical measurements; categorizing each member of the set of subjects as either category (i) or (ii) as follows: (i) a high confidence responder to the therapy or a high confidence non-responder to the therapy, and (ii) a low confidence responder to the therapy, wherein the classifying is performed using the plurality of simulated clinical measurements as input to the classifier that identifies a subject suffering from the a disease as likely responsive or likely non-responsive to the therapy prior to any administration of the therapy to the subject; and validating and/or developing (e.g., training) the classifier using data corresponding to the set of subjects categorized in category (i) and rejecting data corresponding to the set of subjects categorized in category (ii).

In some embodiments, the plurality of clinical measurements comprises tender joint count, swollen joint count, physician global assessment, patient global assessment, patient pain assessment, CRP, or HAQ-DI, or a combination thereof.

In some embodiments, the validating and/or developing comprises modifying the classifier and repeating the categorizing based on the modified classifier (e.g., iterative modification of the classifier).

In some embodiments, the validating and/or developing further comprises training the classifier using data corresponding to the set of subjects categorized in category (i) and rejecting data corresponding to the set of subjects categorized in category (ii), wherein the classifier is a machine learning algorithm.

In another aspect, the present disclosure provides a computer-implemented method of identifying a subject suffering from an autoimmune disease (e.g., rheumatoid arthritis, RA) as responsive or non-responsive to a therapy (e.g., an anti-TNF therapy) prior to any administration of the therapy to the subject, the method comprising: receiving a set of observed values corresponding to a plurality of clinical measurements observed in the subject prior to any administration of the therapy to the subject; identifying the presence or absence of a signal corresponding to a molecular signature response classifier, the classifier having been validated and/or developed (e.g., trained) using the method of any one of the preceding claims; optionally, identifying the subject as a candidate for the therapy (e.g., and/or administering the therapy to the subject) according to the identified presence or absence of the signal; and optionally, identifying the subject as a candidate for an alternative to the therapy (e.g., and/or administering the alternative therapy to the subject) according to the identified presence or absence of the signal.

In some embodiments, the autoimmune disease comprises rheumatoid arthritis, ulcerative colitis, Crohn's disease, juvenile arthritis, psoriatic arthritis, plaque psoriasis, or ankylosing spondylitis, or a combination thereof.

In some embodiments, the therapy comprises anti-TNF therapy. In some embodiments, the anti-TNF therapy comprises infliximab, etanercept, adalimumab, certolizumab pegol, golimumab, or biosimilars thereof, or a combination thereof.

In some embodiments, the therapy comprises an alternative to anti-TNF therapy. In some embodiments, the alternative to anti-TNF therapy comprises rituximab, sarilumab, tofacitinib citrate, leflunomide, vedolizumab, tocilizumab, anakinra, or abatacept, or a combination thereof.

In another aspect, the present disclosure provides a system for validating and/or developing (e.g., training) a classifier that identifies a subject suffering from an autoimmune disease (e.g, rheumatoid arthritis, RA) as responsive or non-responsive to a therapy (e.g., an anti-TNF therapy) prior to any administration of the therapy to the subject, the method, the system comprising: a processor of a computing device; and a memory having instructions stored thereon, wherein the instructions, when executed by the processor, cause the processor to perform any of the methods described herein.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 4A depicts an illustration that every clinical measurement has inherent variability. FIG. 4B depicts a EULAR metric based upon DAS28-CRP disease activity score. FIG. 4C depicts high-confidence scores generated for the EULAR metric by Monte Carlo simulation.

FIG. 5A further depicts a receiver operating characteristic (ROC) curve plotting sensitivity vs. 1-specificity achieving an area under curve (AUC) of 0.606. FIG. 5B depicts a violin plot showing the distribution of DAS28-CRP values for patients with and without a signal of non-response to TNFi therapy.

DETAILED DESCRIPTION

Figure 1:
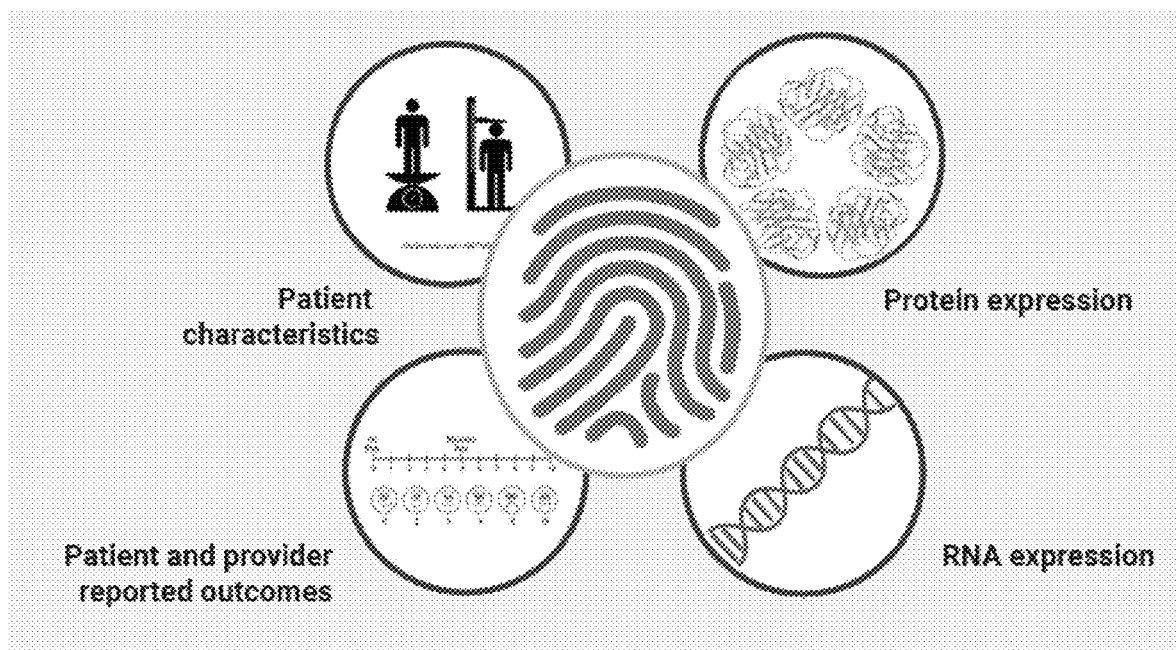
FIG. 1 depicts an example of a molecular signature.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a", "an", and "the" include plural references unless the context clearly dictates otherwise. For example, the term "a feature" includes a plurality of features.

It is contemplated that systems, architectures, devices, methods, and processes of the present disclosure encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific operations, it is contemplated that, additionally, there are articles, devices, systems, and architectures of the present disclosure that consist essentially of, or consist of, the recited components, and that there are processes and methods according to the present disclosure that consist essentially of, or consist of, the recited processing operations.

It should be understood that the order of operation or order for performing some actions is immaterial so long as the present disclosure remains operable. Moreover, two or more operations or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the main body of this document (non-reference) is controlling.

Headers are provided for the convenience of the reader— the presence and/or placement of a header is not intended to limit the scope of the subject matter described herein.

As used herein, the term "subject," generally refers to an entity or a medium that has testable or detectable genetic information. A subject can be a person, individual, or patient. A subject can be a vertebrate, such as, for example, a mammal. Non-limiting examples of mammals include humans, simians, farm animals, sport animals, rodents, and pets. The subject can be a person that has a disease or is suspected of having a disease. The subject may be displaying a symptom(s) indicative of a health or physiological state or condition of the subject, such as a disease, disorder, or condition of the subject. As an alternative, the subject can be asymptomatic with respect to such health or physiological state or condition.

The present disclosure encompasses, among other things, an insight that variability in assessment can introduce uncertainty into clinical data, and that some methods can be utilized to reduce the uncertainty and allow for increased confidence in conclusions drawn from the clinical data. For example, response to therapy is assessed using a multitude of self-assessment inputs, or inputs that are otherwise subjectively measured by a practitioner. Each patient providing a self-assessment input, such as tenderness of joints, or scale of pain, the rating may shift depending on a multitude of factors, which may prohibit meaningful conclusions being drawn from the patient's self-assessment inputs. Moreover, different practitioners can apply different subjective measurements (e.g., apply different amounts of pressure to test for pain in a patient), without intending to inject such variability, meaning that some inputs for a patient may vary from practitioner to practitioner, all other things being equal.

To reduce the amount of variability in clinical data, and thereby produce high confidence metrics that can be used, for example, for training, or validating classification of a patient, the present disclosure provides, among other things, systems and methods for analyzing a set of clinical data, and identifying and removing "low confidence" data, e.g., data that includes too much variability to reliably be used to, for example, train or validate a classifier or classification of a patient. In some embodiments, a result is a data set having high confidence clinical outcomes. The high confidence clinical outcomes are particularly useful in the training and validation of classifiers, e.g., classifiers that predict response or non-response to particular therapies. For example, in some embodiments, a classifier can be validated by classifying a patient as response or non-responsive to a particular therapy, and by analyzing particular clinical characteristics after treatment with therapy, as described herein, validate the classification (e.g., confirm that the classifier correctly identified the patient as responsive or non-responsive to a therapy).

FIG. 1 is a schematic illustrating an example of a molecular signature. A molecular signature is a combination of biological features that capture the genetic makeup and disease behavior of an individual. These features may include RNA, proteins, and other molecular features that reflect the distinctive disease biology of a patient. Like fingerprints, molecular signatures are unique. They reveal how diseases affect each patient differently.

Targeted therapies, like TNF inhibitors, target specific disease-related proteins. Because a disease affects each patient differently, a targeted therapy may work for some patients but not others.

Figure 2:
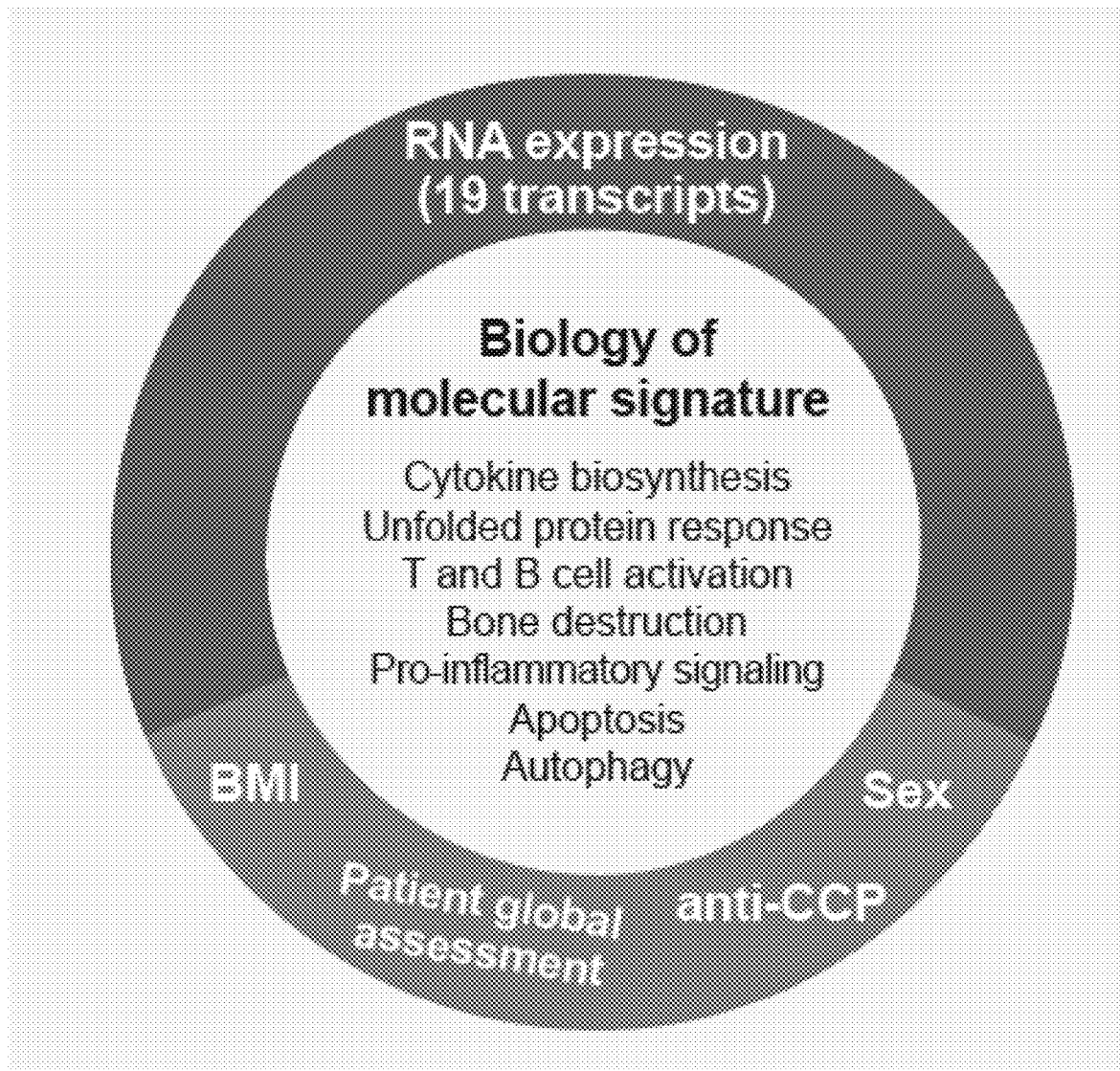
FIG. 2 depicts an example of a 23-feature molecular signature response classifier (MSRC).

FIG. 2 is a schematic illustrating a 23-feature molecular signature response classifier (MSRC) test that may be predictive for inadequate response to TNFi therapies. Patients with a molecular signature of non-response detected were (i) 6.6 times less likely to respond to TNFi therapies; (ii) had a 10.3% response rate to TNFi therapies; and (iii) about 39% of patients tested have a signal of non-response.

Figure 3:
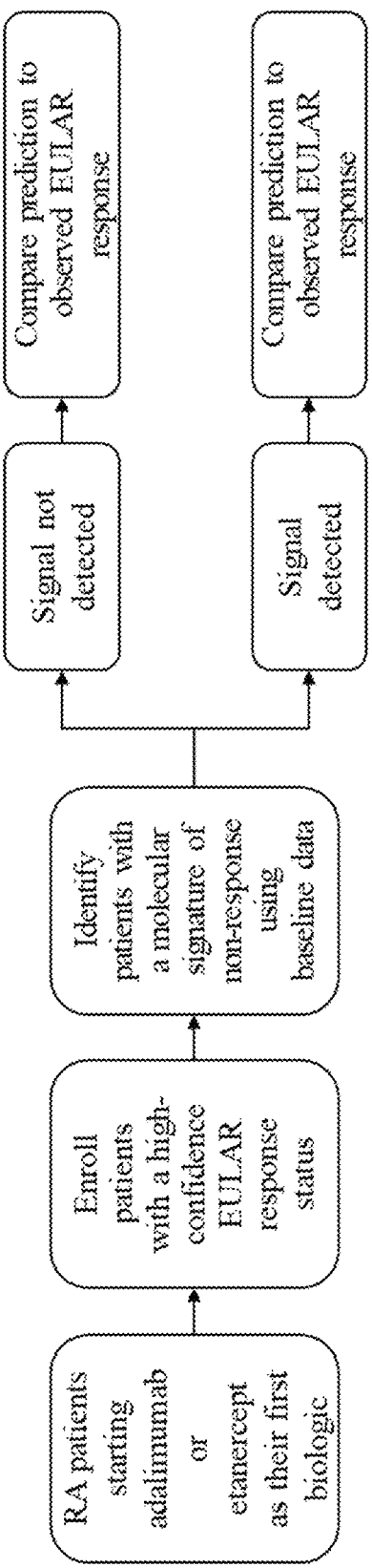
FIG. 3 depicts a block flow diagram illustrating a study design.

FIG. 3 is a block flow diagram illustrating a study design. The study begins with rheumatoid arthritis (RA) patients starting adalimumab or etanercept as their first biologic. Patients with a high-confidence EULAR response status are enrolled. Next, the method identifies patients with a molecular signature of non-response using baseline data. Each prediction for patients for whom a non-response signal is detected is compared to observed EULAR response. Similarly, each prediction for patients for whom a non-response signal is not detected is compared to the observed EULAR response.

In an example, data from a prospective cohort study conducted in the Sint Maartenskliniek (Nijmegen, the Netherlands) of RA patients who started adalimumab or etanercept TNFi as their first biologic were included for validation. Baseline RNA samples and clinical assessments were used to identify patients who had a molecular signature of non-response to TNFi therapy. Outcomes were calculated at six months using DAS28-CRP-based EULAR good response, and high and low confidence responders and non-responders were identified using Monte Carlo simulation with 2,000 repeats and 70% precision cut off. Outcome measurements were blinded for test results. Treatment switch before 6 months was imputed as non-response. Odds ratios and area under the ROC curve (AUC) assessments were used to evaluate the ability of the MSRC test to predict inadequate response at 6 months against EULAR good response criteria.

In this example, a total of 68 out of 88 RA patients were identified to have a high-confidence response status and were included in analyses (Table 1). EULAR good response was observed in 45.5% (31/68) of patients. Patients were stratified according to detection of a molecular signature of non-response with an AUC of 0.61. The odds that a patient with the molecular signature of non-response at baseline failed to achieve a EULAR good response at 6 months was four times greater than that of a patient lacking the molecular signature (odds ratio 4.0, 95% confidence interval 1.2-13.3).

Patient demographics are shown in Table 1.

TABLE 1

Patient demographics

| Characteristic | Value | Characteristic | Value |
|---|---|---|---|
| N | 68 | RF positive, n (%) | 38 (55.9) |
| Age, years (SD) | 57 (11.1) | Initiated adalimumab, n (%) | 11 (16.2) |
| Female, n (%) | 43 (63.2) | Initiated etanercept, n (%) | 57 (83.8) |
| CCP positive, n (%) | 34 (50.0) | | |

Figure 4A:
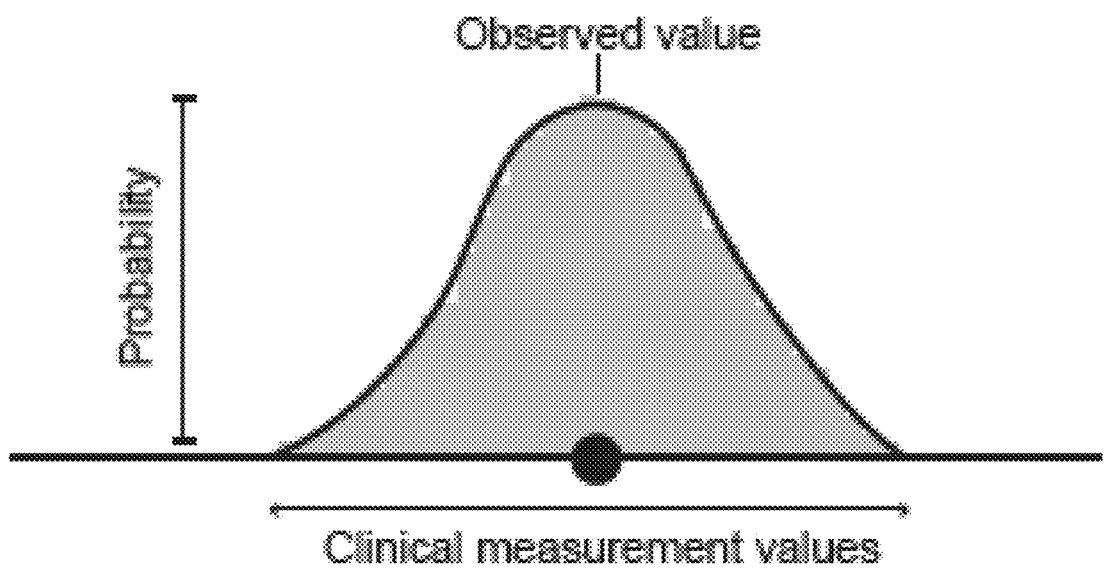
FIGS. 4A, 4B, and 4C depict an example of high-confidence response outcomes.
Figure 4B:
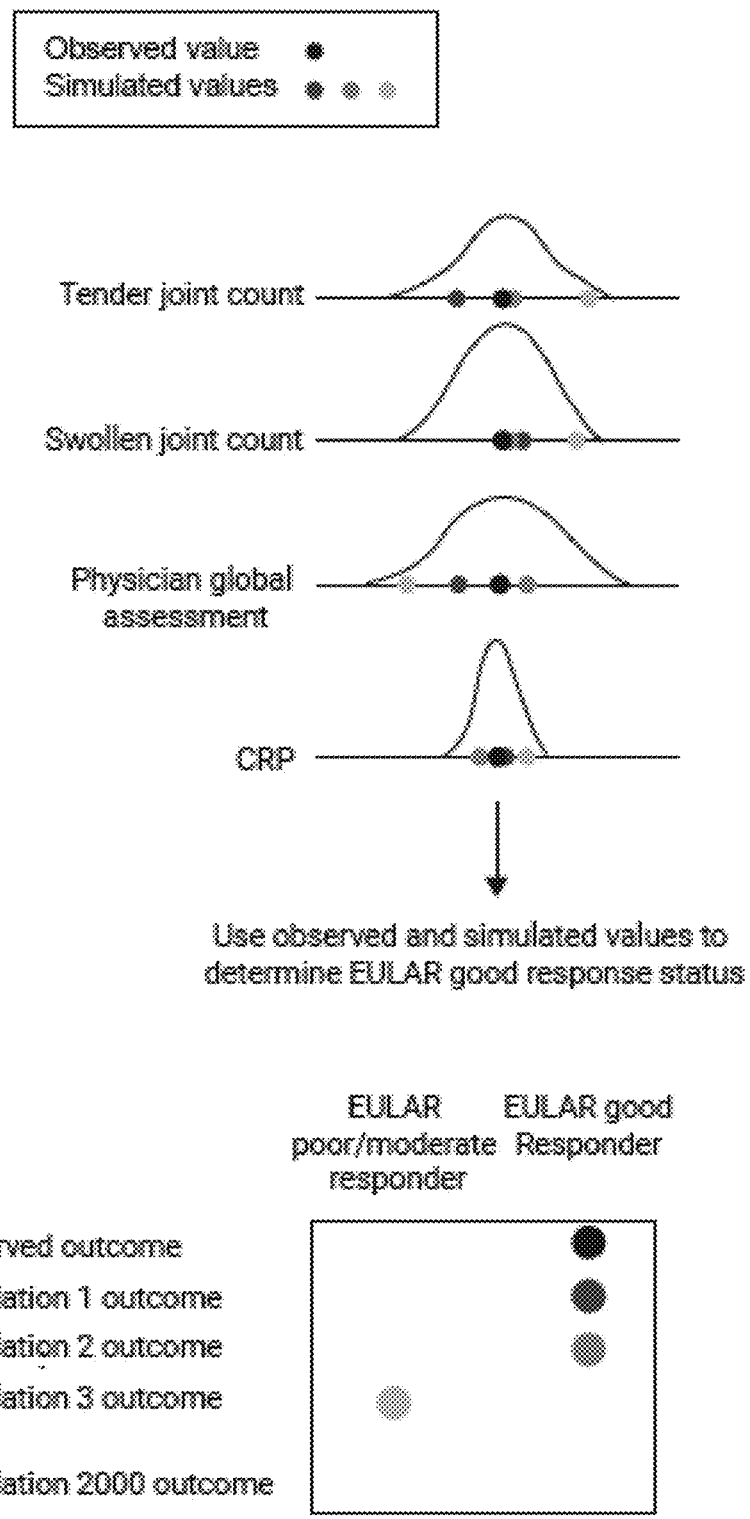
Figure 4C:
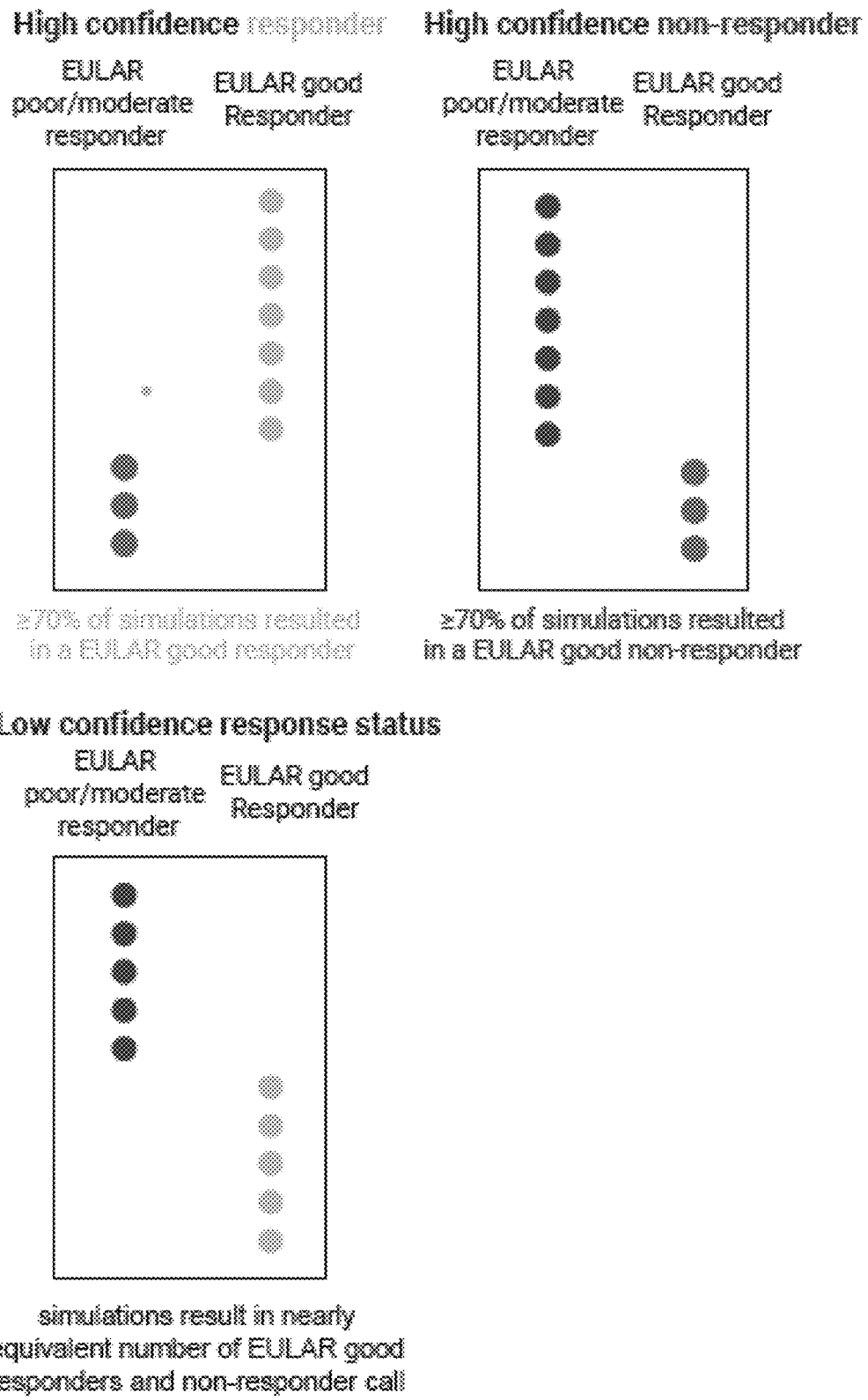

High-confidence response outcomes were identified as illustrated in the schematic of FIGS. 4A-4C. FIG. 4A illustrates that every clinical measurement has inherent variability from measurement error, intra-observer variability, and/or within-subject variability. If the same patient was assessed many times consecutively (e.g., 2000 times), each clinical measurement can be assigned a mean (e.g., average) value and standard deviation. Such repeated measurements can be modeled using observed inter- and/or intra-individual variability and probabilities.

As illustrated in FIG. 4B, the EULAR metric is based upon DAS28-CRP disease activity score, which includes 28 tender joint count, 28 swollen joint count, patient global assessment, and serum C-reactive protein level. Each of these measures have intra-individual variability. See, for example, Table 2. The EULAR metric is categorized into one of three levels: good, moderate, and poor.

TABLE 2

Intra-individual variability of RA disease assessments

| Clinical Assessment | Variability |
|---|---|
| 28 Tender Joint Count | 1.2 |
| 28 Swollen Joint Count | 0.87 |
| Physician Global Assessment | 2.8 |
| Patient Global Assessment | 6.72 |
| Patient Pain Assessment | 5.52 |
| CRP | 1.64 |
| HAQ-DI | 0.01 |

As illustrated in FIGS. 4B and 4C, high-confidence scores were generated for the EULAR metric by Monte Carlo simulation. For 2000 repeats, a simulated value for each component of the EULAR response criterium was assigned. The simulation distributed these values slightly above or below the observed measurement based on probability and published variability statistics. Then, for each set of simulated values and simulation, that patient's EULAR good response status was calculated. When at least 70% of the simulations resulted in the same status, either EULAR good responder or not, that patient was identified as having a high-confidence response status and included in further analysis. In contrast, a low confidence response status indicated that a nearly equivalent number of simulations stated that the patient did or did not achieve a EULAR good response. Such patient samples were excluded because that patient's change in disease activity did not exceed the variability of the component clinical measurements, and thus it cannot be concluded whether or not that patient responded to treatment.

Figure 5A:
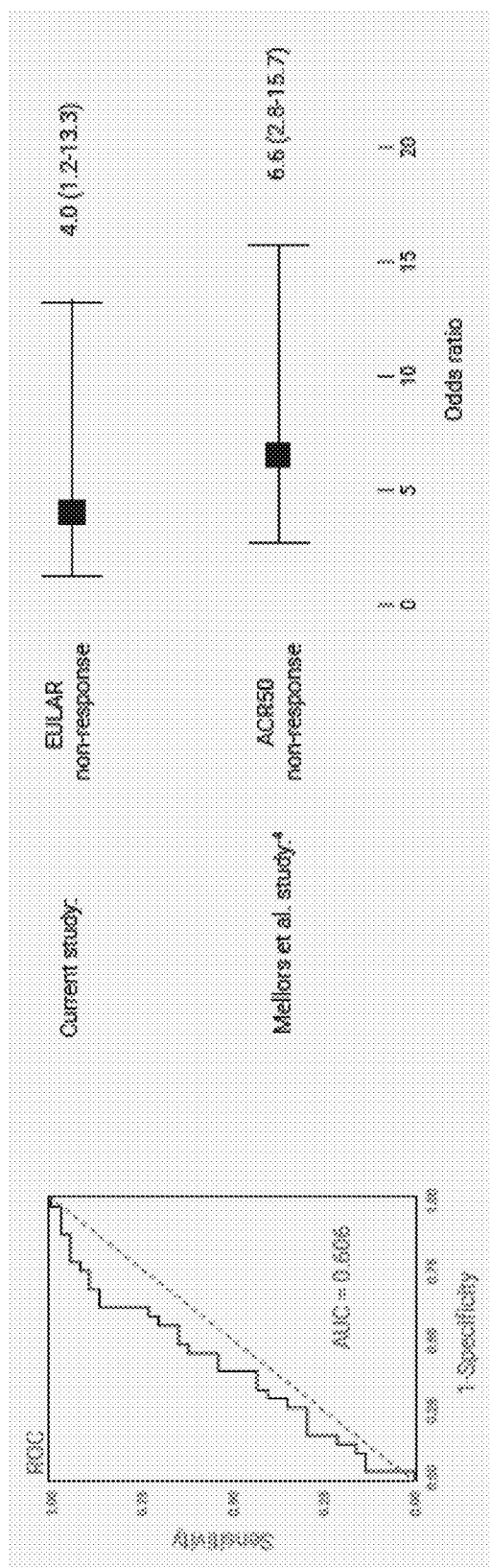
FIGS. 5A and 5B depict an example of the odds that a patient with the molecular signature of non-response at baseline failed to achieve a EULAR good response at 6 months was four times greater than that of a patient lacking the molecular signature.

As shown in FIG. 5A, the odds that a patient with the molecular signature of non-response at baseline failed to achieve a EULAR good response at 6 months was four times greater than that of a patient lacking the molecular signature (odds ratio 4.0, 95% confidence interval 1.2-13.3).

Similarly, as shown in FIG. 5A, the above-described Monte Carlo simulation approach was implemented with respect to the ACR50 metric, which is defined as ≥50% improvement in 28 tender joint count, ≥50% improvement in 28 swollen joint count, and ≥50% improvement in at least three out of five clinical variables (Health Assessment Questionnaire disability index [HAQ-DI], patient pain assessment, patient global assessment, physician global assessment, and serum C-reactive protein level). Simulations were run with 2000 iterations implemented with the respective variation derived for each clinical metric, where each iteration generated a responder or non-responder label for each patient with respect to ACR50. The confidence score was calculated as an aggregated score from 2000 iterations and ranged from 0 to 1, with 0 being a 100% confident responder and 1 being a 100% confident non-responder according to the ACR50 metric. Clinical outcomes data for patients with the simulated responder or non-responder outcomes occurring more than 70% of the time were considered high confidence. Confidence scores around 0.5 were regarded as extreme noisy points.

Figure 5B:
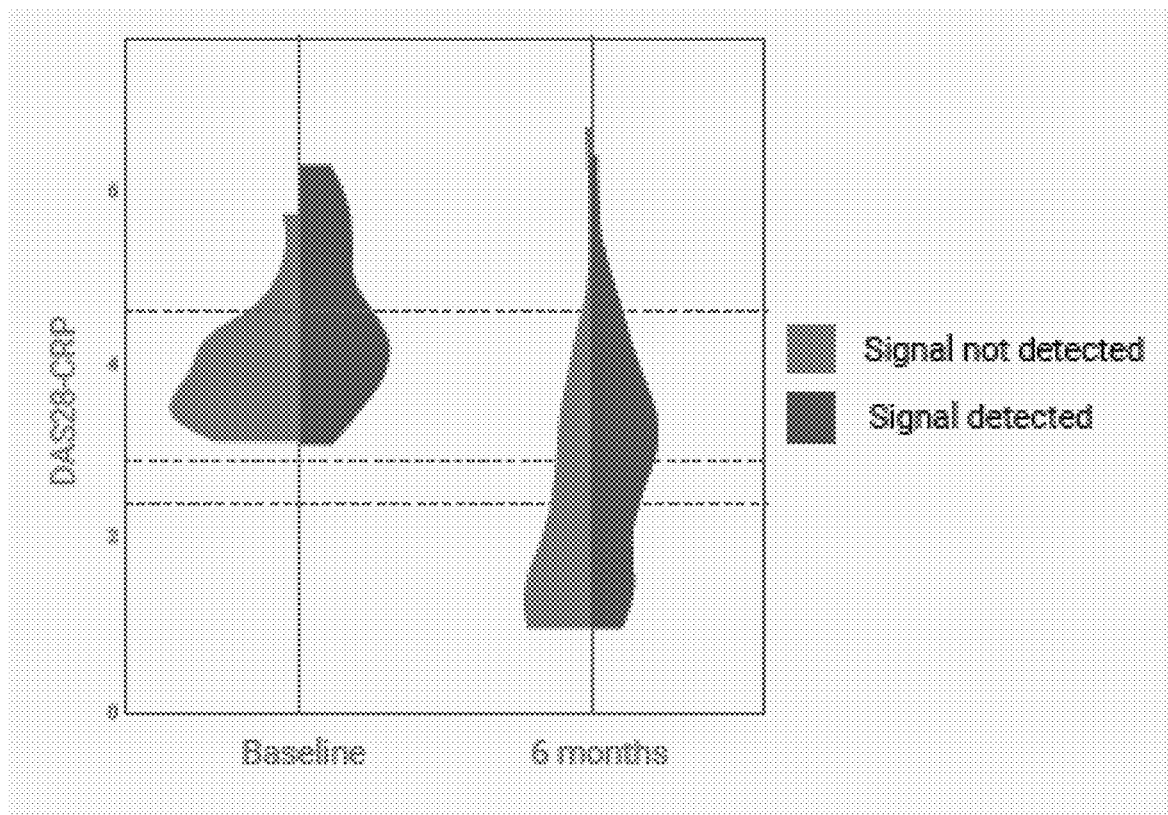

FIG. 5B is a violin plot showing the distribution of DAS28-CRP values for patients with and without a signal of non-response to TNFi therapy. The dotted lines indicate the thresholds dividing remission, low, moderate, and high disease activity. Patients with a baseline molecular signal of non-response showed less improvement in DAS28-CRP in response to TNFi therapy.

In this validation study, the molecular signature of non-response identified patients who did not fulfill the EULAR good response criteria to TNFi therapies. Selection of patients with high-confidence response status may have led to some overestimation of test performance; however, the successful validation of the MSRC test, previously validated for ACR50 inadequate response, for EULAR good response in a tight treat-to-target setting is a beneficial improvement.

This example illustrates that by performing stochastic modeling (e.g., Monte Carlo simulation) as described herein, a neural network-based (e.g., machine learning, or AI-based) classifier was validated and/or developed (e.g., trained) that identifies a subject suffering from an autoimmune disease as likely responsive or likely non-responsive to an anti-TNF therapy prior to any administration of the anti-TNF therapy to the subject. The predictive value of a responsiveness classifier may thereby be validated and/or improved.

Figure 6:
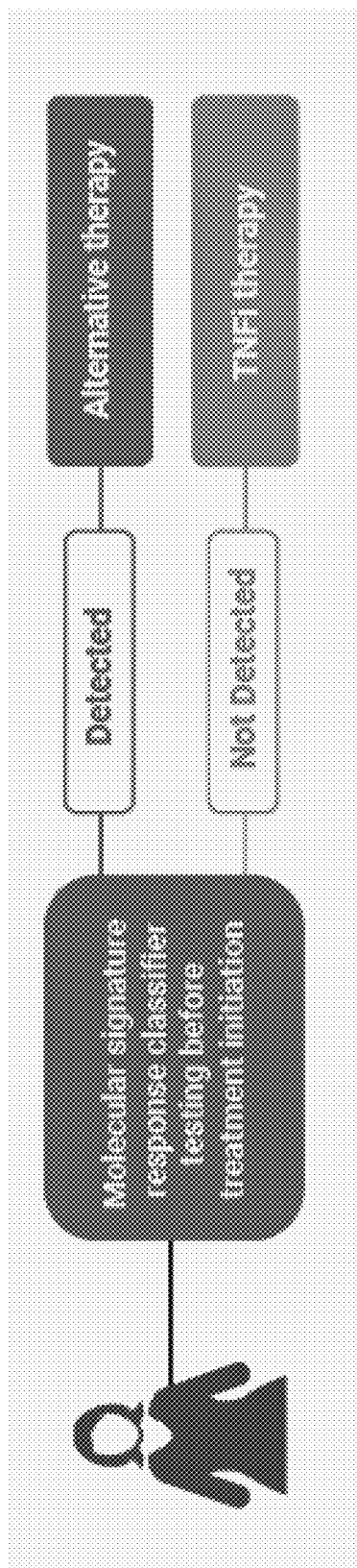
FIG. 6 depicts an example of a method for using a classifier to distinguish between responders and non-responders and to select TNFi therapy or alternative therapy.

Thus, as illustrated in the schematic of FIG. 6, a method comprises performing molecular signature response classifier testing on a subject before treatment initiation, where the classifier has been validated and/or developed using the stochastic approach described herein. If the signature of non-response is detected at the baseline for the patient, an alternative therapy is sought for the patient. If the signature of non-response is not detected, a TNFi therapy may be prescribed and/or administered to the patient. This results in more informed treatment decisions, it may provide a better chance of reaching treatment targets of low disease activity and remission, and it may improve patient experiences and quality of life.

REFERENCES van Nies J A, Krabben A, Schoones J W, Huizinga T W, Kloppenburg M, van der Helm-van Mil A H. What is the evidence for the presence of a therapeutic window of opportunity in rheumatoid arthritis? A systematic literature review. *Ann Rheum Dis* 2014; 73(5): 861-70 is incorporated by reference herein in its entirety.

Schipper L G, Fransen J, den Broeder A A, Van Riel P L. Time to achieve remission determines time to be in remission. *Arthritis Res Ther* 2010; 12(3): R97 is incorporated by reference herein in its entirety.

Cuppen B V, Welsing P M, Sprengers J J, et al. Personalized biological treatment for rheumatoid arthritis: a systematic review with a focus on clinical applicability. *Rheumatology* (Oxford) 2016; 55(5): 826-39 is incorporated by reference herein in its entirety.

Mellors T, Withers J B, Ameli A, et al. Clinical Validation of a Blood-Based Predictive Test for Stratification of Response to Tumor Necrosis Factor Inhibitor Therapies in Rheumatoid Arthritis Patients. *Network and Systems Medicine* 2020; 3(1): 91-104 is incorporated by reference herein in its entirety.

Tweehuysen L, den BroederAA, Schraa K, Netea M G, van den Hoogen F H J, Joosten L A B. Predictive value of ex-vivo drug-inhibited cytokine production for clinical response to biologic DMARD therapy in rheumatoid arthritis. *Clin Exp Rheumatol* 2019; 37(3): 367-72 is incorporated by reference herein in its entirety.

Cheung, P. P., Gossec, L., Mak, A. & March, L. Reliability of joint count assessment in rheumatoid arthritis: a systematic literature review. *Semin Arthritis Rheum* 43, 721-729, doi:10.1016/j.semarthrit.2013.11.003 (2014) is incorporated by reference herein in its entirety.

Uhlig, T., Kvien, T. K. & Pincus, T. Test-retest reliability of disease activity core set measures and indices in rheumatoid arthritis. *Ann Rheum Dis* 68, 972-975, doi:10.1136/ard.2008.097345 (2009) is incorporated by reference herein in its entirety.

Maska, L., Anderson, J. & Michaud, K. Measures of functional status and quality of life in rheumatoid arthritis: Health Assessment Questionnaire Disability Index (HAQ), Modified Health Assessment Questionnaire (MHAQ), Multidimensional Health Assessment Questionnaire (MDHAQ), Health Assessment Questionnaire II (HAQ-II), Improved Health Assessment Questionnaire (Improved HAQ), and Rheumatoid Arthritis Quality of Life (RAQoL). *Arthritis Care Res* (Hoboken) 63 Suppl 11, S4-13, doi:10.1002/acr.20620 (2011) is incorporated by reference herein in its entirety.

Software, Computer System, and Network Environment

Some embodiments described herein make use of computer algorithms in the form of software instructions executed by a computer processor. In some embodiments, the software instructions include a machine learning module, also referred to herein as artificial intelligence software.

As used herein, a machine learning module refers to a computer implemented process (e.g., a software function) that implements one or more specific machine learning algorithms, such as an artificial neural network (ANN), convolutional neural network (CNN), random forest, decision trees, support vector machines, and the like, in order to determine, for a given input, one or more output values. In some embodiments, the input comprises alphanumeric data which can include numbers, words, phrases, or lengthier strings, for example. In some embodiments, the one or more output values comprise values representing numeric values, words, phrases, or other alphanumeric strings. In some embodiments, the one or more output values comprise an identification of one or more response strings (e.g., selected from a database).

For example, a machine learning module may receive as input a textual string (e.g., entered by a human user, for example) and generate various outputs. For example, the machine learning module may automatically analyze the input alphanumeric string(s) to determine output values classifying a content of the text (e.g., an intent).

In some embodiments, machine learning modules implementing machine learning techniques are trained, for example using datasets that include categories of data described herein. Such training may be used to determine various parameters of machine learning algorithms implemented by a machine learning module, such as weights associated with layers in neural networks. In some embodiments, once a machine learning module is trained, e.g., to accomplish a specific task such as identifying certain response strings, values of determined parameters are fixed and the (e.g., unchanging, static) machine learning module is used to process new data (e.g, different from the training data) and accomplish its trained task without further updates to its parameters (e.g., the machine learning module does not receive feedback and/or updates). In some embodiments, machine learning modules may receive feedback, e.g., based on user review of accuracy, and such feedback may be used as additional training data, to dynamically update the machine learning module. In some embodiments, two or more machine learning modules may be combined and implemented as a single module and/or a single software application. In some embodiments, two or more machine learning modules may also be implemented separately, e.g, as separate software applications. A machine learning module may be software and/or hardware. For example, a machine learning module may be implemented entirely as software, or certain functions of a ANN module may be carried out via specialized hardware (e.g., via an application specific integrated circuit (ASIC)).

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, some modules described herein can be separated, combined or incorporated into single or combined modules. Any modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

While the methods and systems of present disclosure has been particularly shown and described with reference to specific preferred embodiments, it should be understood that various changes in form and detail may be made therein without departing from the spirit and scope of the present disclosure.

AI/Machine Learning

Many statistical classification techniques are suitable as approaches to perform the classification described herein. Such methods include but are not limited to supervised learning approaches.

Commonly used supervised classifiers include without limitation the neural network (e.g, artificial neural network, multi-layer perceptron), support vector machines, k-nearest neighbours, Gaussian mixture model, Gaussian, naive Bayes, decision tree and radial basis function (RBF) classifiers. Linear classification methods include Fisher's linear discriminant, logistic regression, naive Bayes classifier, perceptron, and support vector machines (SVMs). Other classifiers for use with methods according to the disclosure include quadratic classifiers, k-nearest neighbor, boosting, decision trees, random forests, neural networks, pattern recognition, Bayesian networks and Hidden Markov models. Other classifiers, including improvements or combinations of any of these, commonly used for supervised learning, can also be suitable for use with the methods described herein.

Classification using supervised methods can generally be performed by the following methodology:

1. Gather a training set. These can include, for example, clinical features described herein from a sample from a patient responding or not responding to anti-TNF therapy. The training samples are used to "train" the classifier.
2. Determine the input "feature" representation of the learned function. The accuracy of the learned function depends on how the input object is represented. Typically, the input object is transformed into a feature vector, which contains a number of features that are descriptive of the object. The features may include clinical features of a patient or subject.
3. Determine the structure of the learned function and corresponding learning algorithm. A learning algorithm is chosen, e.g., artificial neural networks, decision trees, Bayes classifiers or support vector machines. The learning algorithm is used to build the classifier.
4. Build the classifier (e.g., classification model). The learning algorithm is run on the gathered training set. Parameters of the learning algorithm may be adjusted by optimizing performance on a subset (called a validation set) of the training set, or via cross-validation. After parameter adjustment and learning, the performance of the algorithm may be measured on a test set of naive samples that is separate from the training set. The built model can involve feature coefficients or importance measures assigned to individual features.

In some cases, the individual features are clinical features. In some cases, the clinical feature is a normalized value, an average value, a median value, a mean value, an adjusted average, or other adjusted level or value.

Once the classifier (e.g., classification model) is determined as described above ("trained"), it can be used to classify a sample, e.g., clinical features that are analyzed or processed according to methods described herein.

Computer Systems

Figure 7:
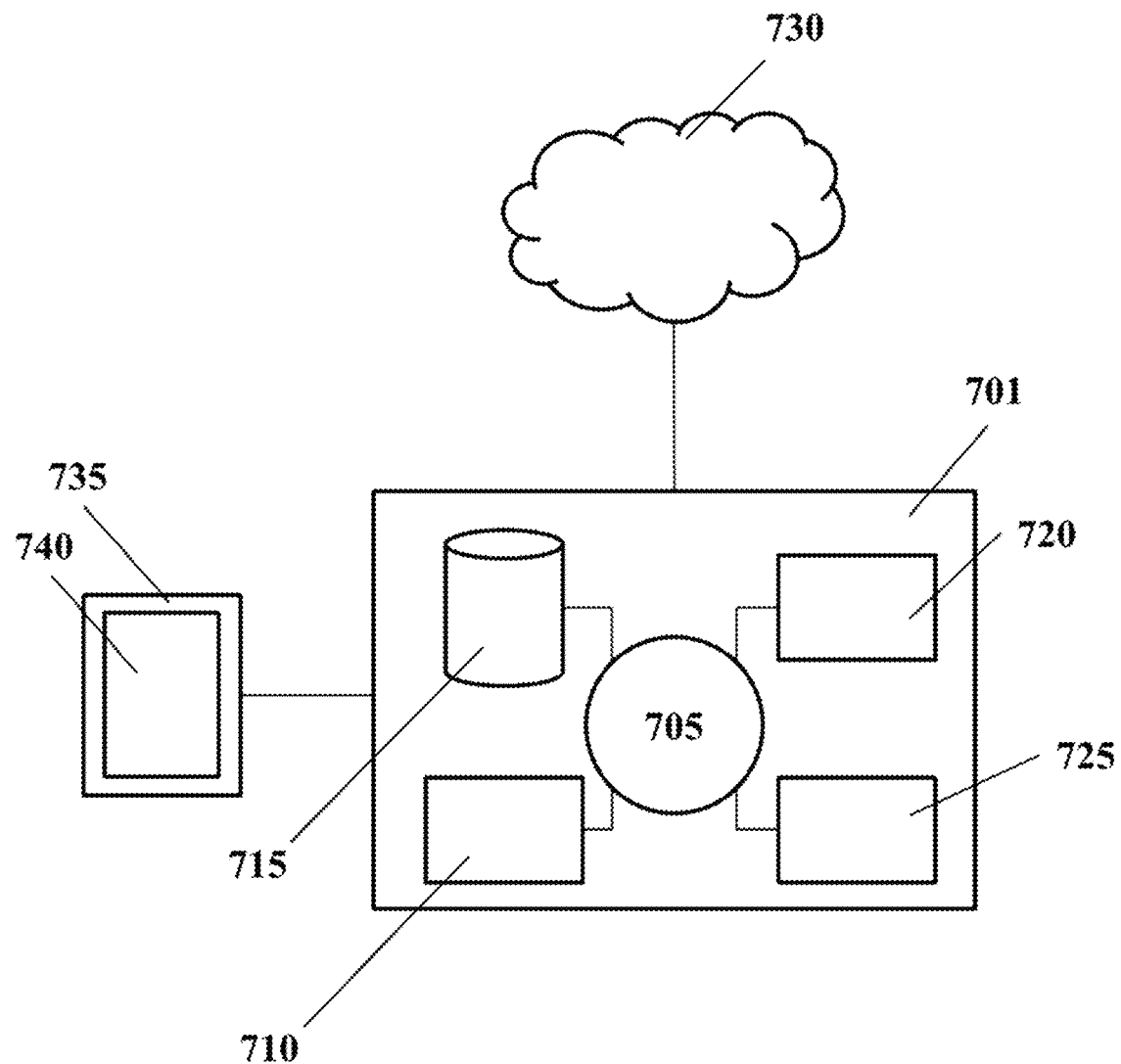
FIG. 7 shows a computer system 701 that is programmed or otherwise configured to implement methods of the present disclosure.

The present disclosure provides computer systems that are programmed to implement methods of the disclosure. FIG. 7 shows a computer system 701 that is programmed or otherwise configured to, for example, assess credibility/confidence of a composite of a plurality of clinical features with inter- or intra-individual variability; and validate or develop a classifier that identifies a subject suffering from a disease, disorder, or condition as responsive or non-responsive to a therapy. The computer system 701 can regulate various aspects of the present disclosure, such as, for example, assessing credibility/confidence of a composite of a plurality of clinical features with inter- or intra-individual variability; and validating or developing a classifier that identifies a subject suffering from a disease, disorder, or condition as responsive or non-responsive to a therapy. The computer system 701 can be an electronic device of a user or a computer system that is remotely located with respect to the electronic device. The electronic device can be a mobile electronic device.

The computer system 701 includes a central processing unit 705 (CPU, also "processor" and "computer processor" herein), which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720, and peripheral devices 725 are in communication with the CPU 705 through a communication bus (solid lines), such as a motherboard. The storage unit 715 can be a data storage unit (or data repository) for storing data. The computer system 701 can be operatively coupled to a computer network 730 ("network") with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries, and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user. Examples of remote computer systems include personal computers (e.g., portable PC), slate or tablet PC's (e.g., Apple® iPad, Samsung® Galaxy Tab), telephones, smartphones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, information to a user of the computer system. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 705. The algorithm can, for example, assess credibility/confidence of a composite of a plurality of clinical features with inter- or intra-individual variability; and validate or develop a classifier that identifies a subject suffering from a disease, disorder, or condition as responsive or non-responsive to a therapy.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for assessing credibility or confidence of a composite of a plurality of clinical features with inter- or intra-individual variability, the method comprising:
   receiving a set of observed values corresponding to a plurality of clinical features observed in a subject that are part of a composite metric, wherein each of the plurality of clinical features has an observed inter- or intra-individual variability;
   generating a plurality of simulated clinical measurements corresponding to each of the observed values, wherein the generating is performed using the corresponding observed inter- or intra-individual variability of the respective clinical features; and
   determining a score or classification of the confidence or credibility of the observed composite metric.

2. The method of claim 1, wherein the composite metric is used in one or more of the following: (i) identifying training or validation sets for building a classifier in diagnostics, (ii) biomarker detection, and (iii) clinical trial cohort identification.

3. The method of claim 1, wherein the composite metric comprises American College of Rheumatology 50 (ACR50), European League Against Rheumatism (EULAR), Crohn's Disease Activity Index (CDAI), or Disease Activity Score-28 with C-reactive Protein Level (DAS28-crp).

4. A computer-implemented method for validating or developing a classifier that identifies a subject suffering from a disease, disorder, or condition as responsive or non-responsive to a therapy prior to any administration of the therapy to the subject, the method comprising:
   receiving for each member of a set of subjects, a set of observed values corresponding to a plurality of clinical measurements observed in the subject, wherein each of the plurality of clinical measurements has an observed inter- or intra-individual variability;
   generating for each member of the set of subjects, a plurality of simulated clinical measurements corresponding to each of the observed values, wherein the generating is performed using the observed inter- or intra-individual variability of each of the plurality of clinical measurements;
   categorizing each member of the set of subjects as either (i) a high confidence responder or high confidence non-responder to the therapy, or (ii) neither a high confidence responder nor high confidence non-responder to the therapy, wherein the classifying is performed using the plurality of simulated clinical measurements as input to the classifier that identifies a subject suffering from the disease as responsive or non-responsive to the therapy prior to any administration of the therapy to the subject; and
   validating or developing the classifier using data corresponding to the set of subjects categorized in category (i) and rejecting data corresponding to the set of subjects categorized in category (ii).

5. The method of claim 4, wherein the disease, disorder, or condition comprises an autoimmune disease or a cancer.

6. The method of claim 4, wherein the disease, disorder or condition is an autoimmune disease.

7. The method of claim 6, wherein the autoimmune disease comprises rheumatoid arthritis, ulcerative colitis, Crohn's disease, juvenile arthritis, psoriatic arthritis, plaque psoriasis, or ankylosing spondylitis, or a combination thereof.

8. A method of treating a subject suffering from a disease, disorder, or condition, the method comprising:
   administering a therapy to the subject who has been assigned a confidence outcome score, wherein the confidence outcome score is derived by:
   analyzing an observed value of one or more clinical characteristics of the disease, disorder, or condition provided by the subject, wherein each of the one or more clinical characteristics has an observed inter- or intra-individual variability;
   calculating a plurality of simulated clinical measurements corresponding to each of the observed values, wherein the calculating is performed using the observed inter- or intra-individual variability of each of the one or more of clinical characteristics; and generating the confidence outcome score from inputs of each of the plurality of simulated clinical measurements, wherein the subject is administered the therapy if the confidence outcome score is a high confidence outcome score.

9. A computer-implemented method for validating or developing a classifier that identifies a subject suffering from a disease, disorder, or condition as responsive or non-responsive to a therapy prior to any administration of the therapy to the subject, the method comprising:
  receiving for each member of a set of subjects, a set of observed values corresponding to a plurality of clinical measurements observed in the subject, wherein each of the plurality of clinical measurements has an observed inter- or intra-individual variability;
  generating for each member of the set of subjects, a plurality of simulated clinical measurements corresponding to each of the observed values, wherein the generating is performed using the observed inter- or intra-individual variability of each of the plurality of clinical measurements;
  categorizing each member of the set of subjects as either category (i) or (ii) as follows: (i) a high confidence responder to the therapy or a high confidence non-responder to the therapy and (ii) a low confidence responder to the therapy, wherein the classifying is performed using the plurality of simulated clinical measurements as input to the classifier that identifies a subject suffering from the disease as responsive or non-responsive to the therapy prior to any administration of the therapy to the subject; and
  validating or developing the classifier using data corresponding to the set of subjects categorized in category (i) and rejecting data corresponding to the set of subjects categorized in category (ii).

10. The method of claim 9, wherein the plurality of clinical measurements comprises tender joint count, swollen joint count, physician global assessment, patient global assessment, patient pain assessment, C-reactive Protein Level (CRP), or Health Assessment Questionnaire Disability Index (HAQ-DI), or a combination thereof.

11. The method of claim 9, wherein the validating or developing comprises modifying the classifier and repeating the categorizing based on the modified classifier.

12. The method of claim 9, wherein the validating or developing further comprises training the classifier using data corresponding to the set of subjects categorized in category (i) and rejecting data corresponding to the set of subjects categorized in category (ii), wherein the classifier is a machine learning algorithm.

* * * * *